US011109939B2

(12) United States Patent
Lorenzo (10) Patent No.: US 11,109,939 B2
(45) Date of Patent: Sep. 7, 2021

(54) INTRAVASCULAR DEVICES WITH RADIOPAQUE BODY MARKERS

(71) Applicant: DePuy Synthes Products, Inc., Raynham, MA (US)

(72) Inventor: Juan Lorenzo, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 270 days.

(21) Appl. No.: 16/441,389

(22) Filed: Jun. 14, 2019

(65) Prior Publication Data
US 2020/0390515 A1  Dec. 17, 2020

(51) Int. Cl.
*A61B 17/221* (2006.01)
*A61F 2/89* (2013.01)
*A61F 2/95* (2013.01)
*A61B 17/22* (2006.01)
*A61B 90/00* (2016.01)

(52) U.S. Cl.
CPC ............ *A61B 90/39* (2016.02); *A61B 17/221* (2013.01); *A61F 2/89* (2013.01); *A61F 2/95* (2013.01); *A61B 2017/2215* (2013.01); *A61B 2017/22041* (2013.01); *A61B 2090/3966* (2016.02); *A61F 2220/0075* (2013.01); *A61F 2250/0039* (2013.01); *A61F 2250/0098* (2013.01)

(58) Field of Classification Search
CPC .. A61F 2/95; A61F 2/962; A61F 2/966; A61F 2/89; A61B 17/221; A61B 2017/2215; A61B 2017/22034
See application file for complete search history.

(56) References Cited

U.S. PATENT DOCUMENTS

| | | | |
|---|---|---|---|
| 6,391,037 B1 | 5/2002 | Greenhalgh | |
| 6,863,685 B2 | 3/2005 | Davila et al. | |
| 6,955,685 B2 | 10/2005 | Escamilla et al. | |
| 7,063,707 B2 | 6/2006 | Bose et al. | |
| 7,846,197 B2 | 12/2010 | Cottone et al. | |
| 8,021,418 B2 | 9/2011 | Gerberding et al. | |
| 8,545,548 B2 | 10/2013 | Lorenzo | |
| 8,852,205 B2 | 10/2014 | Brady et al. | |
| 9,232,992 B2 | 1/2016 | Heidner | |
| 9,232,997 B2 | 1/2016 | Sugimoto et al. | |
| 9,445,829 B2 | 9/2016 | Brady et al. | |
| 9,532,792 B2 | 1/2017 | Galdonik et al. | |
| 9,532,873 B2 | 1/2017 | Kelley | |

(Continued)

OTHER PUBLICATIONS

Extended European Search Report issued in corresponding European Patent Application No. 20 17 9639 dated Nov. 4, 2020.

*Primary Examiner* — Wade Miles
(74) *Attorney, Agent, or Firm* — Troutman Pepper Hamilton Sanders LLP (57) ABSTRACT

An intravascular treatment device is presented having an expandable frame made up of circular struts, straight struts, and bent struts forming a frame with circumference that varies over the length of the frame. Radiopaque markers can be positioned on the bent struts to indicate outer circumferences of the frame along the length of the frame. The device can be a stent or a clot retriever. If the device is a clot retriever, the proximal end of the expandable frame can be attached to a guide wire and the distal end of the expandable frame can be free to slide over the guide wire when the frame moves from a collapsed state to an expanded state and vice versa.

17 Claims, 8 Drawing Sheets

(56) References Cited

U.S. PATENT DOCUMENTS

| | | | |
|---|---|---|---|
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,775,706 B2 | 3/2017 | Peterson et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,693,885 B2 | 7/2017 | Lorenzo |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,052,185 B2 | 8/2018 | Epstein et al. |
| 10,993,731 B2 * | 5/2021 | Leynov ............... A61B 17/221 |
| 2004/0044399 A1 | 3/2004 | Ventura |
| 2004/0167625 A1 * | 8/2004 | Beyar ............... A61B 17/7266 |
| | | | 623/11.11 |
| 2005/0038455 A1 * | 2/2005 | Bates ................. A61F 2/07 |
| | | | 606/153 |
| 2005/0131525 A1 * | 6/2005 | Hartley ............... A61F 2/07 |
| | | | 623/1.15 |
| 2006/0025845 A1 | 2/2006 | Escamilla et al. |
| 2006/0064151 A1 | 3/2006 | Guterman |
| 2007/0021822 A1 * | 1/2007 | Boatman ............. A61F 2/95 |
| | | | 623/1.13 |
| 2007/0282443 A1 * | 12/2007 | Globerman ....... A61B 17/1671 |
| | | | 623/17.11 |
| 2008/0262532 A1 * | 10/2008 | Martin ............ A61B 17/32056 |
| | | | 606/200 |
| 2008/0281350 A1 | 11/2008 | Sepetka |
| 2009/0005853 A1 | 1/2009 | Osman |
| 2009/0287299 A1 * | 11/2009 | Tabor ................. A61F 2/07 |
| | | | 623/1.26 |
| 2010/0324649 A1 | 12/2010 | Mattsson |
| 2011/0224777 A1 * | 9/2011 | Von Oepen ........... A61F 2/91 |
| | | | 623/1.16 |
| 2011/0251674 A1 * | 10/2011 | Schmid ............... A61F 2/90 |
| | | | 623/1.16 |
| 2011/0301690 A1 * | 12/2011 | Giasolli .............. A61F 2/844 |
| | | | 623/1.15 |
| 2012/0116440 A1 * | 5/2012 | Leynov ............. A61B 17/221 |
| | | | 606/200 |
| 2012/0283768 A1 | 11/2012 | Cox et al. |
| 2013/0345739 A1 | 12/2013 | Brady et al. |
| 2014/0135812 A1 | 5/2014 | Divino et al. |
| 2014/0200607 A1 | 7/2014 | Sepetka et al. |
| 2014/0277079 A1 | 9/2014 | Vale et al. |
| 2015/0157329 A1 * | 6/2015 | Rudakov ......... A61B 17/12031 |
| | | | 606/198 |
| 2016/0015402 A1 | 1/2016 | Brady et al. |
| 2016/0022292 A1 | 1/2016 | Stigall et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231646 A1 | 8/2017 | Epstein et al. |
| 2017/0231742 A1 * | 8/2017 | Epstein ................ A61B 34/20 |
| | | | 606/200 |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |

(56) References Cited

U.S. PATENT DOCUMENTS

| | | | |
|---|---|---|---|
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0304041 A1 | 10/2017 | Argentine | |
| 2017/0304097 A1 | 10/2017 | Corwin et al. | |
| 2017/0304595 A1 | 10/2017 | Nagasrinivasa et al. | |
| 2017/0312109 A1 | 11/2017 | Le | |
| 2017/0312484 A1 | 11/2017 | Shipley et al. | |
| 2017/0316561 A1 | 11/2017 | Helm et al. | |
| 2017/0319826 A1 | 11/2017 | Bowman et al. | |
| 2017/0333228 A1 | 11/2017 | Orth et al. | |
| 2017/0333236 A1 | 11/2017 | Greenan | |
| 2017/0333678 A1 | 11/2017 | Bowman et al. | |
| 2017/0340383 A1 | 11/2017 | Bloom et al. | |
| 2017/0340464 A1* | 11/2017 | Kovach | A61F 2/844 |
| 2017/0348014 A1 | 12/2017 | Wallace et al. | |
| 2017/0348514 A1 | 12/2017 | Guyon et al. | |
| 2018/0271547 A1* | 9/2018 | Ulm, III | A61B 17/00234 |
| 2019/0216476 A1* | 7/2019 | Barry | A61B 17/22 |

\* cited by examiner

INTRAVASCULAR DEVICES WITH RADIOPAQUE BODY MARKERS

FIELD OF INVENTION

The present invention generally relates to intravascular therapeutic treatment devices, and more particularly, to expandable stents and clot retrievers with radiopaque body markers.

BACKGROUND

Intravascular devices such as stents and clot retrievers come in a variety of shapes, sizes, and constructions. Considerations in stent and clot retriever design include the goal of the treatment, location of the treatment site, and geometry of the treatment site. A stent or a clot retriever can require a certain amount of flexibility to navigate blood vessels to reach a treatment site, and in the case of the clot retriever, retract through the blood vessels with the clot intact. A stent can require a certain amount of structural integrity to support a body lumen or an embolic implant, and a clot retriever can require a certain amount of structural integrity to expand around or through a clot. A stent or a clot retriever can require a certain amount of conformability to appropriately expand within curved vasculature. Finally, a certain amount of radiopacity can also be required so that a physician can properly position an intravascular device.

Flexibility, structural integrity, conformability, and radiopacity are often competing design goals. Unfortunately, in many applications, radiopaque materials do not have optimal material properties to meet the design goals of flexibility, structural integrity, and conformability, and devices made of materials conducive to the goals, such as Nitinol and other memory shape metals can have poor radiopacity, making it difficult for physicians to visualize the positioning of the device during treatment. To meet the competing goals, generally, devices are constructed primarily with a material such as Nitinol to achieve flexibility, structural integrity, and conformability, and radiopaque material is added. Incorporating radiopaque material into the body of intravascular devices is challenging, however, especially in devices designed for extreme flexibility, structural integrity, conformability, or small size.

There therefore exists a need for improved or alternative intravascular devices having radiopaque markers.

SUMMARY

It is an object of the present invention to provide systems, devices, and methods to meet the above-stated needs. Generally, it is an object of the present invention to provide an intravascular treatment device having an expandable frame made up of circular struts, straight struts, and bent struts forming a frame with circumference that varies over the length of the frame. Radiopaque markers can be positioned on the bent struts to indicate outer circumferences of the frame along the length of the frame. The device can be a stent or a clot retriever. If the device is a clot retriever, the proximal end of the expandable frame can be attached to a guide wire and the distal end of the expandable frame can be free to slide over the guide wire when the frame moves from a collapsed state to an expanded state and vice versa.

An example intravascular treatment device can include an elongated guide and an expandable framework that can move from a collapsed configuration to an expanded configuration. In the collapsed configuration, the framework can be sized to traverse through a lumen of a catheter, and in the expanded configuration, the framework can be sized to extend radially within a lumen of a blood vessel.

The expandable framework can be constructed of ring struts, central struts, and bent struts. The ring struts can each be positioned to encircle the elongated guide such that each ring strut has an adjacent ring strut in the proximal direction and another adjacent ring strut in the distal direction, with the exception of the distal most and the proximal most ring struts, which each have only one adjacent ring strut. The central struts can be positioned to join each ring strut to one adjacent ring strut, and the bent struts can be positioned to join each ring strut to its opposite adjacent ring strut. When the expandable framework is in the collapsed configuration, the ring struts can each be in a constricted position around the elongated guide and the bent struts can each be in a longitudinally elongated shape. When the expandable framework moves from the collapsed configuration to the expanded configuration, the ring struts can each move to a radially expanded position around the elongated guide, the central struts can maintain essentially the same shape as when the expandable framework is in the collapsed configuration, and the bent struts can each move to a radially expanded shape.

When the expandable framework is in the expanded configuration, groups of bent struts can be positioned to define outer circumferences of the expandable framework. The circumferences defined by the groups of bent struts can differ from one group of bent struts to the next such that one group of bent struts can define a circumference that is smaller than another circumference defined by a different group of bent struts. The expandable frame can include several groups of bent struts including a distal group near the distal end of the frame, a proximal group near the proximal end of the frame, and one or more intermediate groups between the proximal group and the distal group. The distal and the proximal groups can each define a circumference that respectively are larger than any circumference defined by the intermediate groups of bent struts. Alternatively, each of the groups of bent struts can define a circumference that is substantially equal to the circumference defined by each of the other groups of bent struts.

When the expandable framework is in the expanded configuration, groups of central struts can be positioned to each define an inner circumference of the expandable framework. At least one of the circumferences defined by at least one of the groups of central struts can be smaller than at least one of the circumferences defined by at least one of the groups of bent struts. Groups of central struts having smaller circumferences can be positioned between groups of bent struts having larger circumferences so that the expandable framework has a variable circumference that transitions between larger circumferences defined by the bent struts and smaller circumferences defined by the central struts along some or all of its length.

When the expandable framework is in the expanded configuration, the expandable body can have a first circumference defined by a first group of bent struts and a second circumference defined by a first group of central struts positioned adjacent to the first group of bent struts. The second circumference can measure smaller than the first circumference. A second group of bent struts can be positioned adjacent the first group of central struts to define a third circumference. A second group of central struts can be positioned adjacent the second group of bent struts to define a fourth circumference. The fourth circumference can be about equal to the second circumference. The first circumference can measure more than about two times the second circumference. The third circumference can be about equal to the first circumference. Alternatively, the third circumference can be smaller than the first circumference and larger than both the second circumference and the fourth circumference.

The intravascular treatment device can further include radiopaque markers secured to the bent struts by threads on the bent struts. The radiopaque markers can be positioned on groups of bent struts to define a respective circumference of each group of bent struts.

The expandable framework can have a proximal end and a distal end. The proximal end can be affixed to the elongated guide. The distal end can be slidably movable over the elongated guide.

An example clot capture device can move from a delivery configuration to a deployed configuration. In the delivery configuration, the clot capture device can be sized to traverse through a lumen of a catheter. In the deployed configuration, the clot capture device can be sized to extend radially within a lumen of a blood vessel.

The clot capture device can include ring struts, central struts, and bent struts. At least some of the ring struts can be joined to two adjacent ring struts, one distally adjacent and the other proximally adjacent. Those ring struts can be joined to one of the adjacent ring struts by one or more central struts and to the other adjacent ring strut by a group of one or more bent struts. When the clot capture device is in the delivery configuration, the ring struts can have a constricted circumference and the bent struts can have a longitudinally elongated shape. When the clot capture device moves to the deployed configuration, the ring struts can expand to an expanded circumference, the bent struts can expand to a radially expanded shape, and the central struts can maintain essentially the same shape as when the clot capture device is in the delivery configuration.

When the clot capture device is in the deployed configuration, each group of bent struts can define a respective circumference that each measure greater than each respective expanded circumference of the ring struts. In other words, the expanded circumference of each group of ring struts can measure smaller than each circumference of defined by the expanded groups of bent struts.

When the clot capture device is in the deployed configuration, the device can include two groups of bent struts each defining a respective circumference that are each about equal to each other. The device can further include a third group of bent struts having a circumference that is smaller than the respective circumferences defined by the other two groups. The third group can be positioned in between the other two groups, distal to one group, and proximal to the other.

When the clot capture device is in the delivery configuration, ring struts connected by a group of bent struts can be positioned a certain distance apart. This distance between the ring struts can shrink as the clot capture device moves from the delivery configuration to the deployed configuration. When the clot capture device is in the delivery configuration, ring struts connected by central struts can be positioned a certain distance apart. This distant can remain approximately equal as the clot capture device moves from the delivery configuration to the deployed configuration.

The clot capture device can include radiopaque markers attached to some or all of the bent struts. The radiopaque markers can provide an indication of the collapsed circumference of the clot capture device when the clot capture device is in the delivery configuration. The radiopaque markers can provide an indication of an expanded circumference of the clot capture device when the clot capture device is in the deployed configuration.

Some or all of the bent struts can be threaded. The radiopaque markers can be secured to the bent struts by the threads.

The clot capture device can have an expandable frame that is constructed from the ring struts, central struts, and bent struts. The clot capture device can also include a guide wire that extends through a central axis of the expandable frame. The guide wire can be affixed to a proximal end of the expandable frame. A distal end of the expandable frame can be free to move over the guide wire as the frame expands and/or contracts.

An example method can include one or more of the following steps that can be performed in various orders, combinations, and together with additional steps not listed here. An expandable frame can be positioned to encircle a guide wire. The frame can be attached to the guide wire at an attachment site near a proximal end of the frame. The frame can be collapsed around the guide wire in a delivery configuration sized to traverse a lumen of a catheter. The frame can be expanded from the delivery configuration to a deployed configuration. The attachment of the frame to the guide wire at the attachment site can be maintained as the frame expands from the delivery configuration to the deployed configuration. At least part of the frame can slide over the guide wire as the frame expands from the delivery configuration to the deployed configuration.

Radiopaque markers can be positioned to define larger circumferences in the variable circumference when the frame is in the deployed configuration.

In the deployed configuration, the frame can be shaped to have a length measurable from its distal end to its proximal end and a variable circumference that changes over at least part of the length from a first circumference, to a second, smaller circumference less than half the first circumference, to a third circumference larger than the second circumference, and back again to the second circumference.

The frame can be formed from ring struts, longitudinal struts, and bendable struts. Each ring strut can be positioned to encircle the guide wire. The ring struts can be spaced along the length of the frame such that, with the exception of the ring struts at the proximal and distal ends of the frame, each ring strut can have two adjacent neighboring ring struts, one on each side. Each ring strut can be connected to one neighbor by bendable struts. Each ring strut can be connected to the other neighbor by longitudinal struts. When the frame is expanded from the delivery configuration to the deployed configuration, each ring strut can expand radially away from the guide wire, the shape of each longitudinal strut can be maintained as essentially constant, and each bendable strut can be extended radially away from the guide wire.

Radiopaque markers can be positioned to provide an indication of circumferences around groups of bendable struts when the frame is in the deployed configuration.

At least a portion of the frame can be expanded within a clot. At least a portion of the clot can be captured within the frame.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

Visualization of Nickel Titanium (Nitinol) stents or clot retrievers while in clinical use can be difficult as the radiopacity of Nitinol is poor. Various exemplary intravascular therapeutic treatment devices are described herein to improve visualization of clot retrievers and stents. In general, a device can have a collapsible frame 110 with radiopaque markers 150 attached thereto and a delivery system 200 positioned to deliver the frame to a treatment site. A system of radiopaque markers attached to the body of a self-expanding Nickel Titanium (Nitinol) stent or clot retrieval device can enable visualization under fluoroscopy of the device's outer surface. Radiopaque markers can allow the user to determine the device outer body conformance to a blood vessel wall as in the case of a stent. In the case of a clot retrieval device, the markers can allow the user to determine the location of the clot over the body of the device and can aid in the process of retrieving the clot from a blood vessel.

Figure 1:
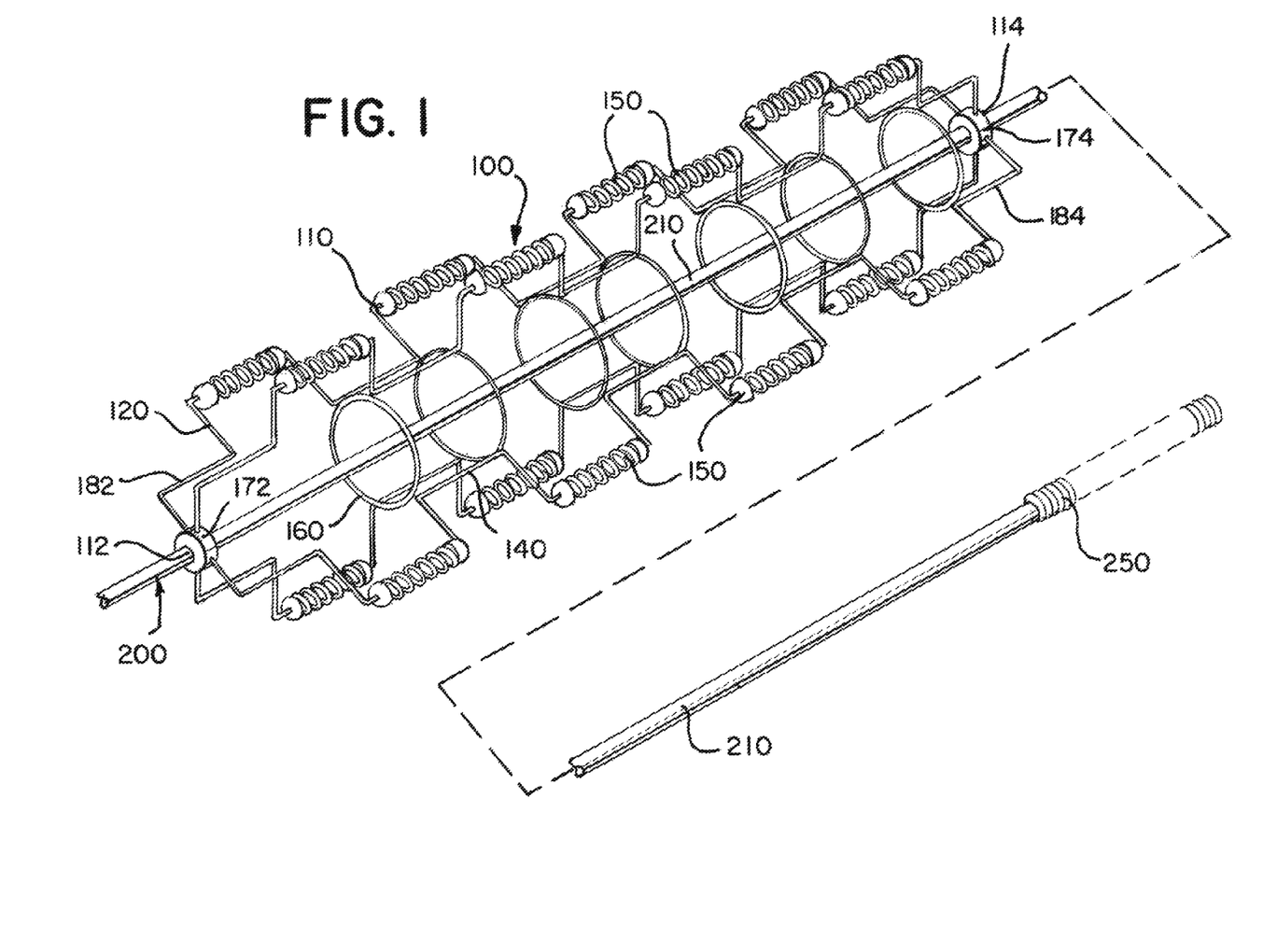
FIG. 1 is a perspective view illustration of an exemplary intravascular treatment device in an expanded configuration according to aspects of the present invention.
Figure 2:
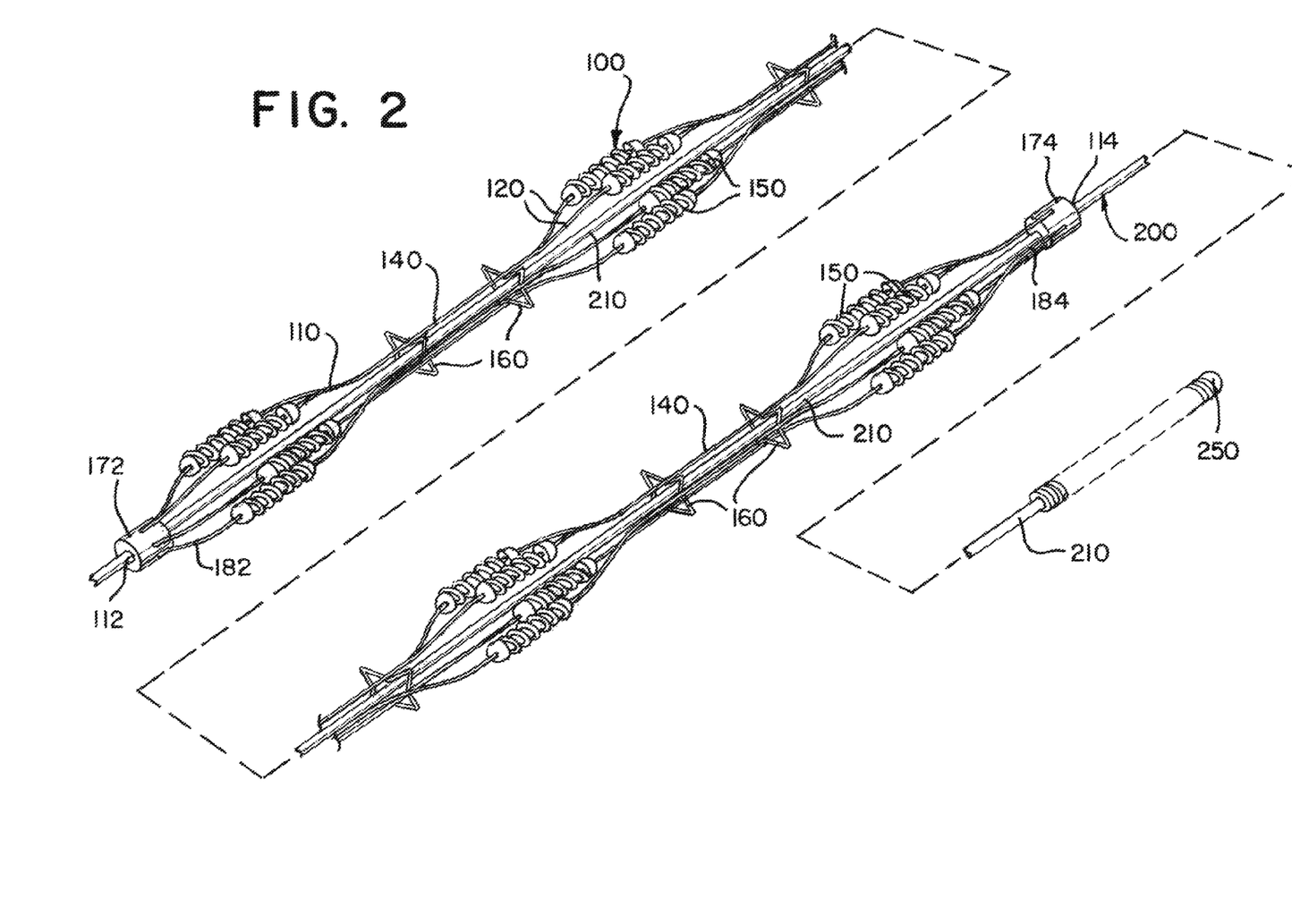
FIG. 2 is a perspective view illustration of the exemplary intravascular treatment device illustrated in FIG. 1 in a collapsed or delivery configuration.
Figure 3A:
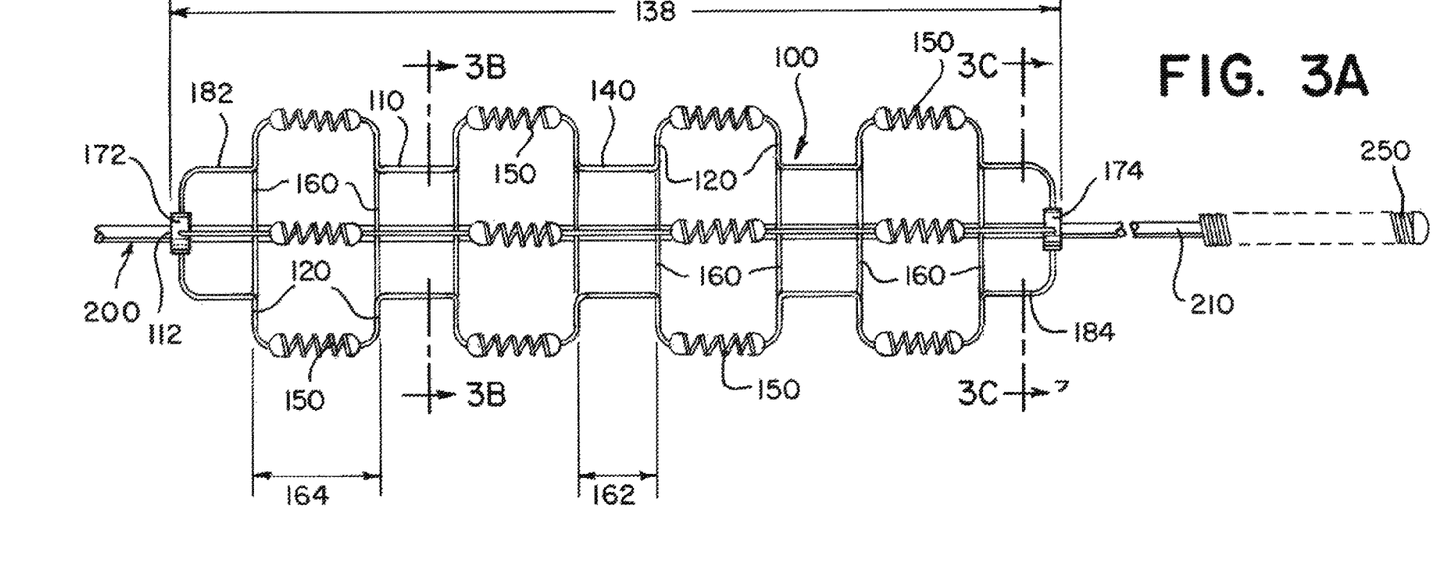
FIG. 3A is a side view illustration of the expanded exemplary intravascular treatment device illustrated in FIG. 1.
Figure 3B:
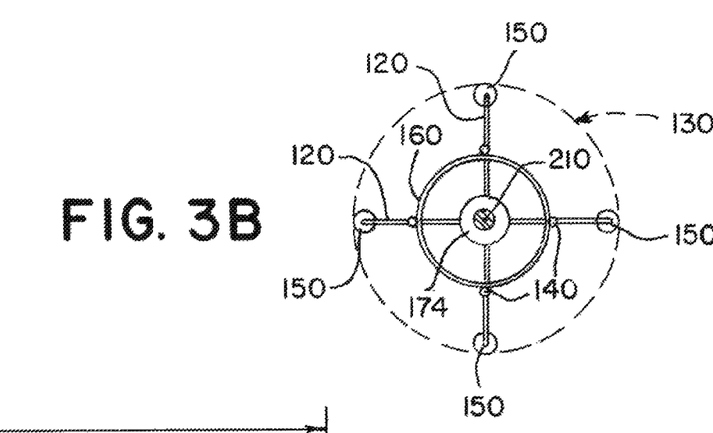
FIG. 3B is a cross sectional view of the exemplary intravascular treatment device as indicated in FIG. 3A.
Figure 3C:
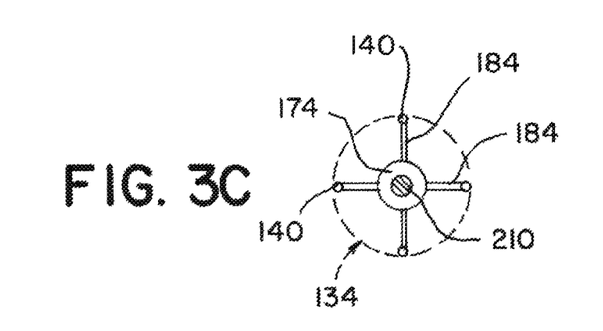
FIG. 3C is a cross sectional view of the exemplary intravascular treatment device as indicated in FIG. 3A.
Figure 4A:
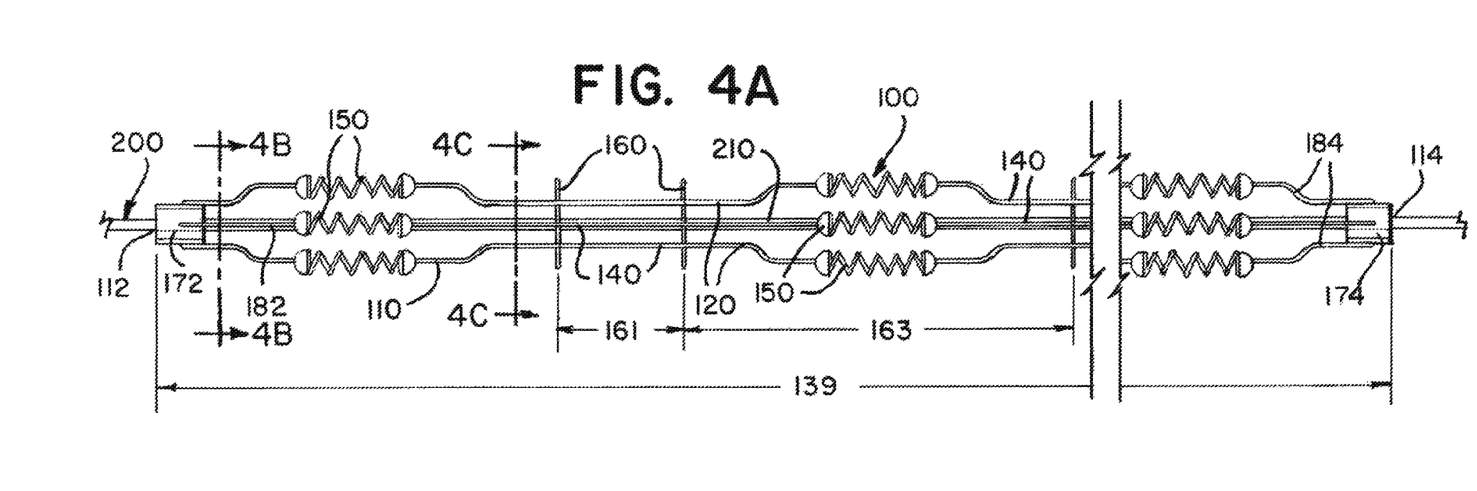
FIG. 4A is a side view illustration of the collapsed exemplary intravascular treatment device illustrated in FIG. 2.
Figure 4B:
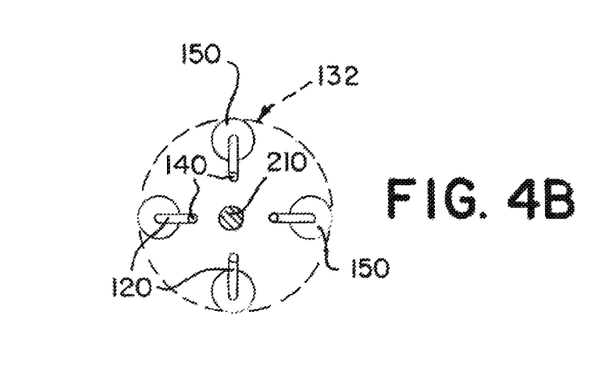
FIG. 4B is a cross sectional view of the exemplary intravascular treatment device as indicated in FIG. 4A.
Figure 4C:
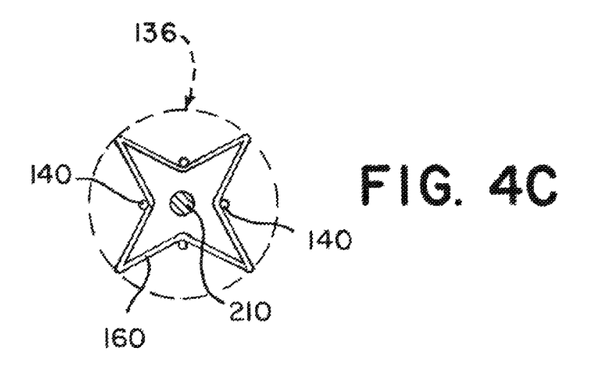
FIG. 4C is a cross sectional view of the exemplary intravascular treatment device as indicated in FIG. 4A.

FIG. 1 is a perspective view illustration of an example intravascular treatment device 100 in an expanded configuration. The frame 110 can be collapsed to fit through a lumen of a catheter and expanded within a blood vessel as part of an intravascular treatment. The frame 110 can include memory shape material such that the frame has a predetermined expanded shape such as illustrated in FIG. 1 and a deformed collapsed shape such as illustrated in FIG. 2. FIG. 3A is a side view of the intravascular treatment device 100 when expanded and FIGS. 3B and 3C are cross sectional views of the expanded intravascular treatment device 100 as indicated in FIG. 3A. FIG. 4A is a side view of the intravascular treatment device 100 when collapsed and FIGS. 4B and 4C are cross sectional views of the collapsed intravascular treatment device 100 as indicated in FIG. 4A When the device 100 is deployed during treatment, the frame 110 can expand from a collapsed configuration such as illustrated in FIGS. 2 and 4A through 4C toward the expanded configuration, or predetermined shape such as illustrated in FIGS. 1 and 3A through 3C. The frame 110 can be inhibited from expanding fully to the predetermined shape by geometry of the blood vessel in which it is deployed. In some applications, the frame 110 can advantageously expand through an obstruction such as a clot. In other applications, the frame 110 can be inhibited from expanding fully to the predetermined shape by a clot, plaque, or obstruction. The frame 110 can therefore expand to a deployed configuration when expanded in a blood vessel that is based on the predetermined shape of the expanded configuration and potentially also shaped by the treatment site in which it is deployed.

Referring collectively to FIGS. 1 through 4C, the expandable frame 110 of the device can include bent struts 120, circular struts 160, and straight central struts 140. The device 100 can include a delivery system 200 that includes a guide wire 210. The proximal end 112 of the frame 110 can be affixed to the guide wire 210 and the distal end 114 of the frame 110 can be free to slide over the guide wire 210. The proximal end 112 of the frame 110 can include an attachment feature 172 such as glue, weld, or other known attachment type to affix the frame 110 to the guide wire 210. The distal end 114 of the frame can include a sliding collar 174 positioned to slide longitudinally along the guide wire 210.

In the expanded or deployed configuration as illustrated in FIGS. 1 and 3A through 3C, circular struts 160 can be positioned along a length 138 of the frame 110. The circular struts 160 can encircle the guide wire 110. The guide wire 110 can extend through the frame 110 along a central axis of the frame, passing through each circular strut 160 at or near the center of the circle made by each circular strut 160. The circular struts 160 can each be oriented in planes parallel to each other and perpendicular to the central axis of the frame 110 and the guide wire 210.

Each circular strut 160, with the exception of the distal most circular strut 160 and the proximal most circular strut 160, can have two adjacent neighbor circular struts 160— one distal neighbor and one proximal neighbor. The distal most circular strut 160 can have only a proximal neighbor. The proximal most circular strut 160 can have only a distal neighbor. The frame 110 can include longitudinally extending struts 140, 120 connecting each circular strut 160 to its neighbors.

In the expanded or deployed configuration, the longitudinally extending struts 140, 120 can include straight struts 140 that are essentially straight connectors extending between adjacent circular struts 160 and bent struts 120 that extend both radially outward and longitudinally between adjacent circular struts 160. Each circular strut 160 can be connected to one of its neighbors by straight struts 140 and the other of its neighbors by bent struts 120.

Groups of straight struts 140 can extend between adjacent circular struts 160 to define an inner circumference 134 of the frame 110 when the frame 110 is in the deployed or expanded configuration. The adjacent circular struts 160 can respectively have circumferences that are approximately equal to each other. The inner circumference 134 defined by the group of straight struts 140 extending between the adjacent circular struts 160 can be equal to, or about equal to the circumference of the circular struts 160. As illustrated in FIG. 1, groups of straight struts 140 can each respectively define an inner circumference 134 that is about equal to the inner circumference 134 defined by every other group of straight struts 140.

The adjacent circular struts 160 connected by a group of straight struts 140 can be separated by a distance 162 when the frame 110 is in the expanded or deployed configuration. The distance 162 can be approximately equal to the length of each substantially straight strut 140 in the group of straight struts 140 connecting the adjacent circular struts 160.

Each group of straight struts 140 can include four straight struts 140 positioned equidistant around the inner circumference 134. It is contemplated that as few as 3 straight struts 140 and as many as 6 straight struts 140 can form a group of straight struts 140. Fewer straight struts 140 in a group can provide greater flexibility in the frame 110 and larger openings for ease of extending through a clot. More straight struts 140 in a group can provide greater structural integrity of the frame 110 and smaller openings for increased containment or grip on a clot.

The frame 110 can be constructed such that all of the groups of straight struts 140 include an equal number of straight struts 140. Alternatively, the frame 110 can be constructed to include groups of straight struts 140 having differing numbers of straight struts 140 from each other to vary the flexibility and opening sizes in the frame 110 along the length 138 of the frame 110. For instance, it can be advantageous to have groups of fewer straight struts 140 near the center of the length 138 so that the frame 110 can more easily extend through a clot and groups of more straight struts 140 near the distal end of the frame 110 to more effectively contain the clot as the clot is pulled proximally through vasculature by the device 100.

When the frame 110 is in the deployed configuration, the bent struts 120 can each extend radially outward from a circular strut 160, bend about 90°, extend longitudinally—substantially parallel to the guide wire 210 or the central axis of the frame 110, bend again about 90°, and extend radially inward. The bent struts 120 can be "U" shaped such that the legs of the "U" are directed radially from the frame 110 centerline or the guide wire 210 and the trough of the "U" is situated the furthest away from the frame centerline or the guide wire 210.

On some or all of the bent struts 120, radiopaque markers can be attached centrally along the bent strut 120. When the frame 110 is in the expanded or deployed configuration, the radiopaque markers can be positioned at the trough of the "U" shape on some or all of the bent struts 120. In other words, the radiopaque markers 150 can be attached to some or all of the bent struts 120 at the portion of each bent strut 120 that extends longitudinally—substantially parallel to the guide wire 210 or the central axis of the frame 110.

When the frame 110 is in the deployed configuration, groups of bent struts 120 can extend to each define a respective outer circumference 130 of the frame 110. Multiple bent struts 120 in a group of bent struts can include radiopaque markers 150 attached thereto such that the radiopaque markers 150 indicate a circumference 130 of the group of bent struts.

Some or all of the bent struts 120 can be threaded, and the radiopaque markers 150 can be shaped to fit over the threads on the bent struts 120.

The frame 110 can have alternating groups of bent struts 120 and groups of straight struts 140 along its length 138. The groups of bent struts 120 can each define respective outer circumferences 130 that are larger than each respective inner circumference 134 defined by each group of straight struts 134. The frame 110 can thereby have a variable circumference along its length 138 that alternates between the larger outer circumferences 130 defined by the groups of bent struts 120 and the smaller inner circumferences 134 defined by the groups of straight struts 140.

Each group of bent struts 120 can include four bent struts 120 positioned equidistant around the outer circumference 130. It is contemplated that as few as 3 bent struts 120 and as many as 6 bent struts 120 can form a group of bent struts 120. Fewer bent struts 120 in a group can provide greater flexibility in the frame 110 and larger openings for ease of extending through a clot. More bent struts 120 in a group can provide greater structural integrity of the frame 110 and smaller openings for increased containment or grip on a clot.

The frame 110 can be constructed such that all of the groups of bent struts 120 include an equal number of bent struts 120. Alternatively, the frame 110 can be constructed to include groups of bent struts 120 having differing numbers of bent struts 120 from each other to vary the flexibility and opening sizes in the frame 110 along the length 138 of the frame 110. For instance, it can be advantageous to have groups of fewer bent struts 120 near the center of the length 138 so that the frame 110 can more easily extend through a clot and groups of more bent struts 120 near the distal end of the frame 110 to more effectively contain the clot as the clot is pulled proximally through vasculature by the device 100.

The bent struts 120 can be aligned longitudinally with the central struts 140 to form a contiguous longitudinal extension along a majority of the length 138 of the frame 110. FIGS. 1 through 4C illustrate the frame 110 having four such contiguous longitudinal extensions each including four bent struts 120 and three straight struts 140. The bent struts 120 and straight struts 140 can be positioned in an alternating fashion as illustrated and separated by connections to circular struts 160.

The frame 110 can also include proximal end struts 182 and distal end struts 184. The proximal end struts 182 can be shaped to connect the frame 110 to the proximal attachment node 172. The distal end struts 184 can be shaped to connect the frame 110 to the distal sliding attachment 174. The proximal end struts 182 and the distal end struts 184 can respectively be longitudinally aligned with bent struts 120 and straight struts 140. The aforementioned contiguous longitudinal extensions can include a proximal end strut 182 at the proximal end 112 of the frame 110 and a distal end strut 184 at the distal end 114 of the frame 110. The contiguous longitudinal extensions can each thereby extent the entirety, or vast majority of the length 138, 139 of the frame 110 in the expanded or collapsed configuration.

In the delivery/collapsed configuration, the frame 110 can be collapsed to fit through a lumen of a catheter. In the collapsed configuration, the frame 110 can have a length 139 that is longer compared to the length 138 of the frame 110 in the expanded configuration.

The circular struts 160 can be collapsed to a collapsed circumference 136 that is smaller than the circumference 134 of the circular struts 160 in the expanded configuration. Adjacent circular struts 160 connected by straight struts 140 can be separated by a distance 161 when the frame 110 is in the collapsed configuration that is approximately equal to the distance 162 between the circular struts 160 when the frame 110 is in the expanded configuration. The bent struts 120 can be elongated when the frame 110 is in the collapsed configuration. Adjacent circular struts 160 connected by bent struts 120 can be separated by a distance 163 when the frame 110 is in the collapsed configuration that is longer than the length 164 between the adjacent circular struts 160 in the expanded or deployed configuration. When the frame 110 is in the collapsed configuration, groups of bent struts 120 can respectively define a circumference 132 that is smaller than the circumference 130 defined by each respective group of bent struts 120 in the expanded configuration.

Comparing the length 138 of the frame 110 in the expanded configuration to the length 139 of the frame 110 in the collapsed configuration, the length 139 in the collapsed configuration can be primarily extended due to the longitudinal extension of the bent struts 120.

The frame 110 can have a predetermined shape illustrated such as illustrated in FIGS. 1 and 3A through 3C and a deformed shape such as illustrated in FIGS. 2 and 4A through 4C. The frame 110 can be heat set in the predetermined shape and collapsed to the deformed shape for delivery through a catheter. The frame 110 can be deformed by stretching the bent struts 120 distally so that they are substantially straight and crimping the circular struts 160.

The delivery system 200 can include a radiopaque coil 250 at its distal end. As illustrated in FIGS. 2 and 4A through 4C, the length 139 of the frame 110 can be extended in the collapsed configuration to extend along the guide wire 210 between the proximal attachment node 172 and the radiopaque coil 250. The delivery system 200 can therefore be sized with a distance between the proximal attachment node 172 and the radiopaque coil 250 sufficient to allow the frame 110 to extend so that the bent struts 120 can be sufficiently collapsed to fit within a lumen of a catheter.

When the device 100 is deployed, it can move from the deformed shape such as illustrated in FIGS. 2 and 4A through 4C toward the predetermined shape such as illustrated in FIGS. 1 and 3A through 3C. When the bent struts 120 move from being substantially straight when the frame 110 is in the collapsed configuration, to the "U" shape when the frame 110 is in the expanded configuration, the free distal end 114 of the frame 110 can slide proximally over the guide wire 210. When moving toward the predetermined shape, the circular struts 160 can expand radially.

Figure 5A:
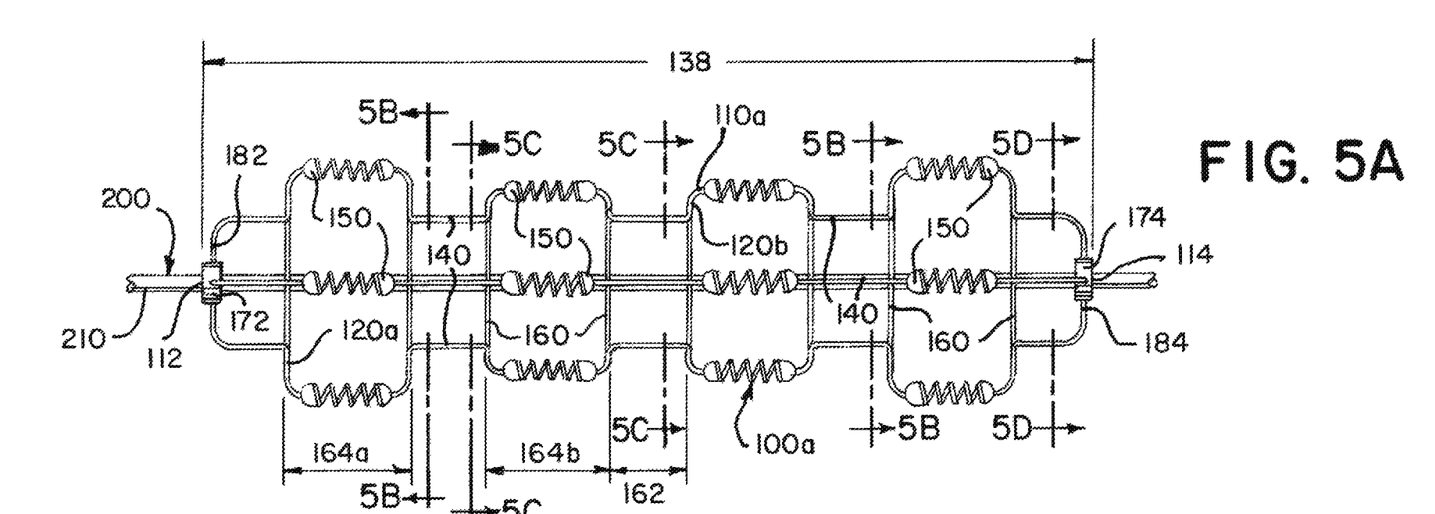
FIG. 5A is a side view illustration of an exemplary intravascular treatment device having an alternative expanded or deployed configuration according to aspects of the present invention.
Figure 5B:
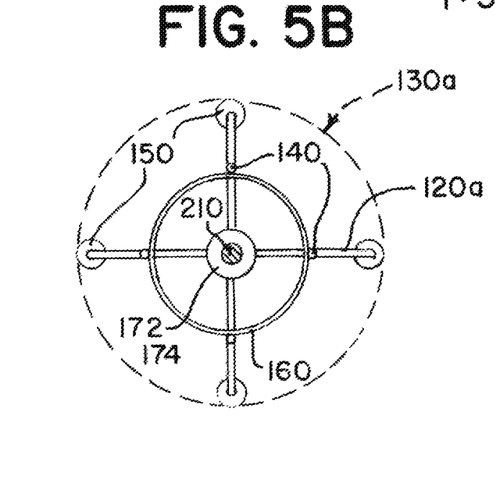
FIG. 5B is a cross sectional view of the exemplary intravascular treatment device as indicated in FIG. 5A.
Figure 5C:
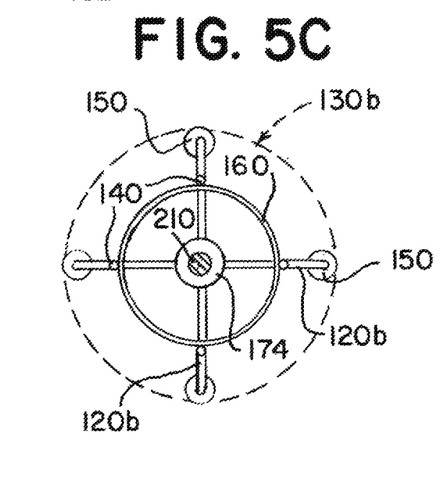
FIG. 5C is a cross sectional view of the exemplary intravascular treatment device as indicated in FIG. 5A.
Figure 5D:
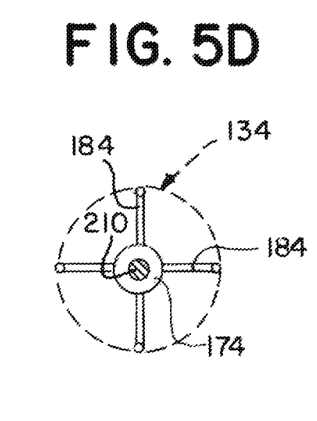
FIG. 5D is a cross sectional view of the exemplary intravascular treatment device as indicated in FIG. 5A.

FIGS. 5A through 5D are illustrations of an example intravascular treatment device 100a having an alternative expanded or deployed configuration. Like reference numerals indicate similar or identical elements that are common between the device 100 illustrated in FIGS. 1 through 4C and the device 100a illustrated in FIGS. 5A through 5D. FIG. 5A is a side view of the device 100a and FIGS. 5B through 5D are cross sectional views of the device 100a as indicated in FIG. 5A.

Comparing the example device 100 illustrated in FIGS. 1 through 4C to the example device 100a illustrated in FIGS. 5A through 5D, the expandable frame 110a of the device 100a in FIGS. 5A through 5D includes groups of bent struts 120a, 120b that define differing outer circumferences 130a, 130b, whereas, groups of bent struts 120 illustrated in FIGS. 1 through 4C define circumferences 130 that are approximately equal. The device 100a illustrated in FIGS. 5A through 5D can include a first group of bent struts 120a defining a first circumference 130a and a second group of bent struts 120b defining a second circumference 130b smaller than the first circumference 130a. A group of bent struts 120b defining a smaller circumference 130b can be positioned centrally along the length 138 of the frame 110a. The group of bent struts 120b defining the smaller circumference 130b can be positioned between two groups of bent struts 120a each respectively defining larger circumferences 130a.

It can be advantageous to position one or more groups of bent struts 120b each respectively defining a smaller circumference 130b centrally along the length 138 of the frame 110a so that the bent struts 120b in those groups don't compress as far longitudinally when the frame 110a is collapsed or extend as far radially as the frame 110a is expanding. This can result in a frame 110a that is not as long when compressed in a delivery configuration compared to a frame 110 having equally sized bent struts 120 such as illustrated in FIG. 1.

The smaller central bent struts 120b can define smaller openings in the frame 110a which can provide a better grip on a clot. Larger bent struts 120a at the distal and proximal ends 112, 114 of the frame 110a can serve to confine a clot longitudinally.

The device 100a illustrated in FIGS. 5A through 5D can be elongated and compressed similar to as described in relation to the device 100 illustrated in FIG. 2. When expanded as illustrated in FIG. 5A, adjacent circular struts 160 connected by a first group of larger circumference bent struts 120a can be separated by a first distance 164a, and adjacent circular struts 160 connected by a second group of smaller circumference bent struts 120b can be separated by a second distance 164b. The first and the second distance 164a, 164b can be about equal to each other. When the frame 110a is collapsed for delivery through a catheter, the bent struts 120a, 120b can be extended longitudinally such that the adjacent circular struts 160 connected by the first group of bent struts 120a are separated by a third distance that is greater than the first distance and the adjacent circular struts 160 connected by the second group of bent struts 120b are separated by a fourth distance that is greater than the second distance and less than the third distance. In other words, when the frame 110a is in the delivery configuration, the first group of bent struts 120a can be longer than the second group of bent struts 120b and both groups of bent struts 120a, 120b can be longitudinally longer than they were when in the expanded configuration.

The delivery system 200 can be dimensioned such that the frame 110a has sufficient room to expand longitudinally between the proximal attachment node 172 and the radiopaque coil 250 so that the frame 110a can be collapsed to fit within a microcatheter.

Figures 6, 7A, 7B, 7C:
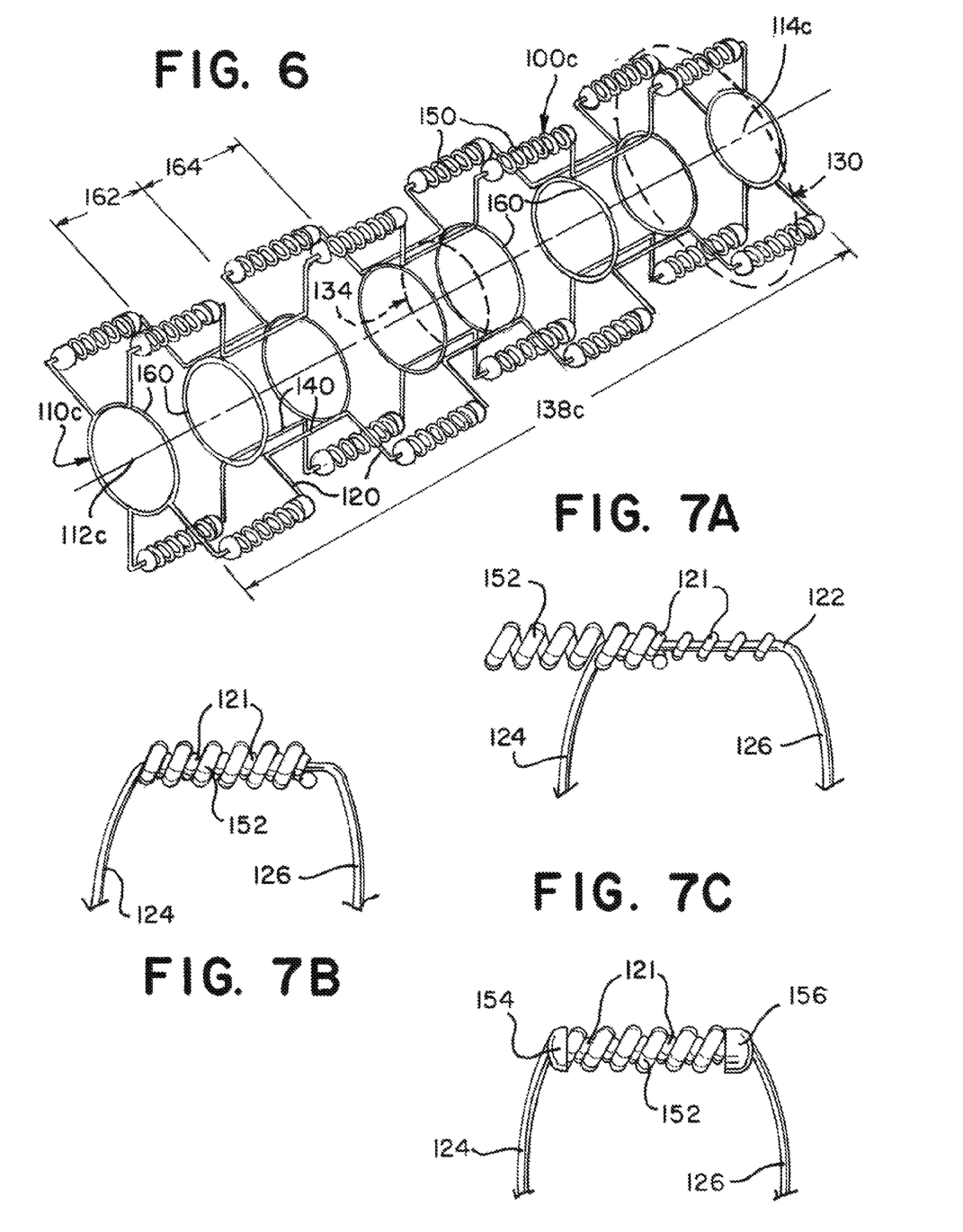
FIG. 6 is a perspective view illustration of an exemplary stent in an expanded configuration according to aspects of the present invention.
FIG. 7A to 7C are illustrations of a radiopaque marker assembly and a threaded bent strut according to aspects of the present invention.

FIG. 6 is an illustration of a stent 100c having an expandable frame 110c having a structure similar to the frame 100 illustrated in FIGS. 1 through 4C. Like reference numerals indicate similar or identical elements that are common between the device 100 illustrated in FIGS. 1 through 4C and the stent 100c illustrated in FIG. 6.

Comparing the example device 100 illustrated in FIGS. 1 through 4C to the stent 100c illustrated in FIG. 6, the expandable frame 110c of the stent 100c in FIG. 6 need not be attached to a guide wire 210, therefore the frame 110c is illustrated absent a delivery system 200, attachment feature 172, proximal connecting struts 182, distal sliding collar 174, and distal connecting struts 184. The proximal end 112c and the distal end 114c of the frame 110c can be terminated by circular struts 160 as illustrated or by other expandable and/or anchoring structures as would be appreciated and understood by a person of ordinary skill in the art. The strut 100c can have a length 138c in the expanded configuration that is measurable from the proximal end 112c of the frame 110c to the distal end 114c of the frame.

Several delivery systems are known for delivering a stent to a blood vessel and such delivery systems are not described in detail herein. The stent 100c can be delivered by a delivery system as would be appreciated and understood by a person of ordinary skill in the art. The stent 100c can be collapsed for delivery through a catheter similar to as illustrated in FIG. 2.

FIGS. 7A to 7C are illustrations of a radiopaque marker assembly 150 and a threaded bent strut 120. Some or all of the bent struts 120, 120a, 120b in the example devices 100, 100a, 100c presented herein can include threads 121 such as illustrated in FIGS. 7A through 7C.

Radiopaque markers 150 can have a helical coil 152 and end attachments 154, 156. Each helical coil 152 can be twisted onto the threads 121 of a respective bent strut 120 as illustrated in FIG. 7A. The bent strut 120 can be bent to have a first strut leg 124, a second strut leg 126, and a threaded portion 122 extending between the first strut leg 124 and the second strut leg 126. A bend can separate the first strut leg 124 from the threaded portion 122 of the strut 120. The bend can be shaped to facilitate the helical coil 152 of the radiopaque marker 150 being twisted onto the threads 121 as illustrated in FIG. 7A.

Once the helical coil 152 is positioned as illustrated in FIG. 7B, the ends of the coil 152 can be affixed to the strut 120 with end attachments 154, 156. The end attachments 154, 156 can be a weld, glue, or other known attachment.

Figure 8:
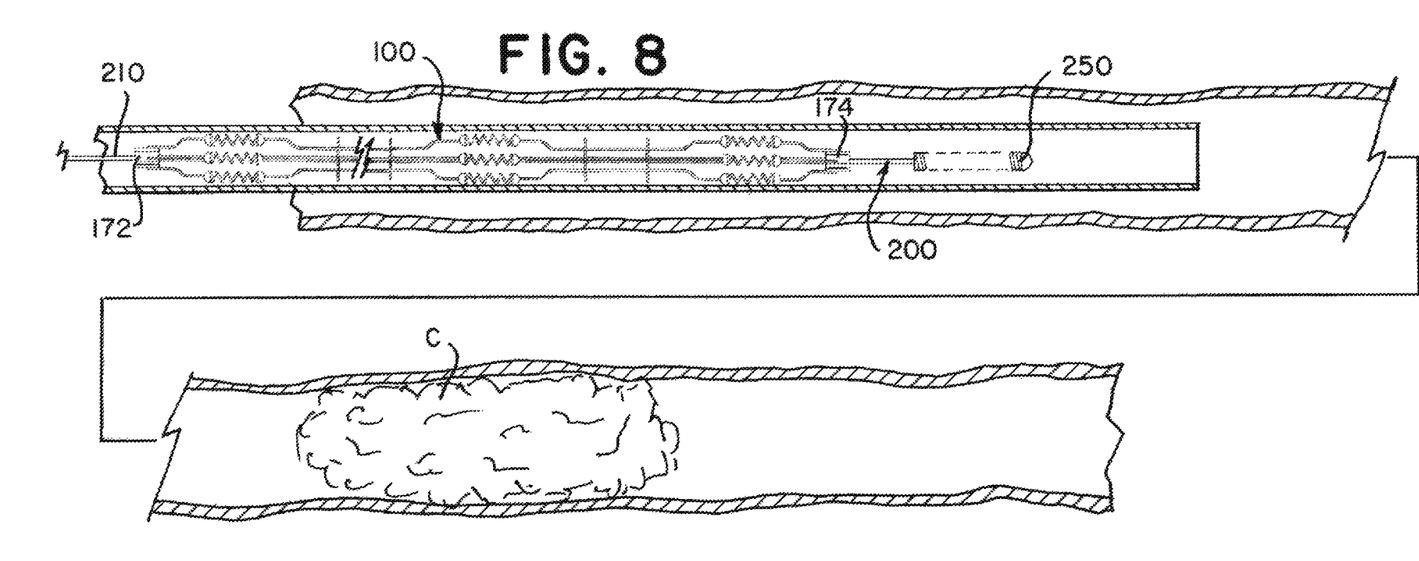
FIG. 8 is an illustration of an exemplary intravascular treatment device being delivered through vasculature to a clot according to aspects of the present invention.
Figure 9:
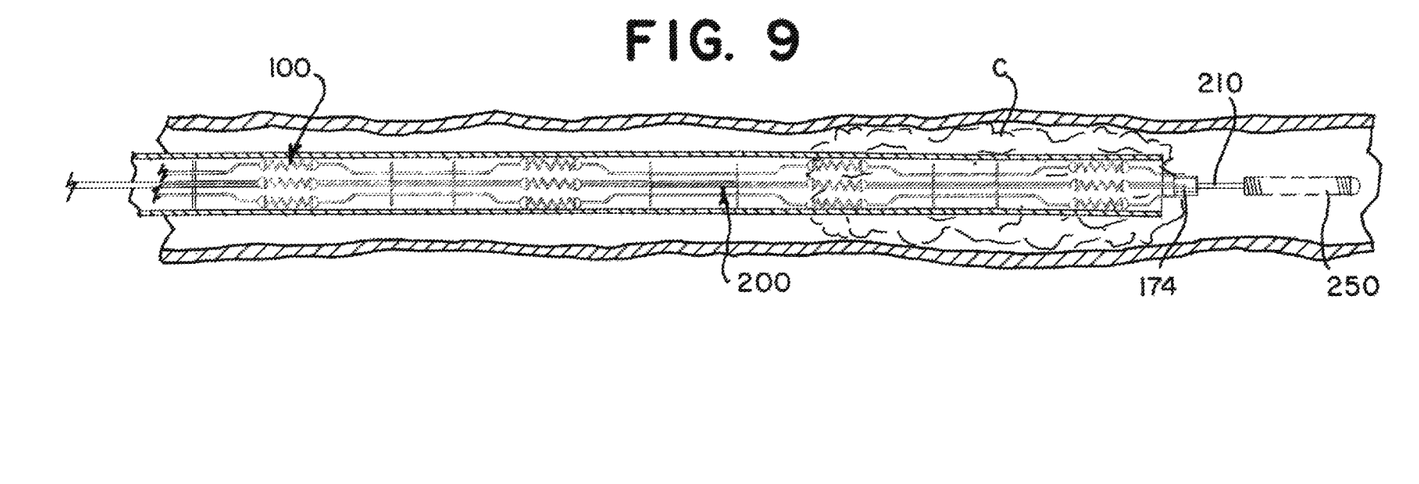
FIG. 9 is an illustration of the intravascular treatment device illustrated in FIG. 8 approaching the clot.
Figure 10:
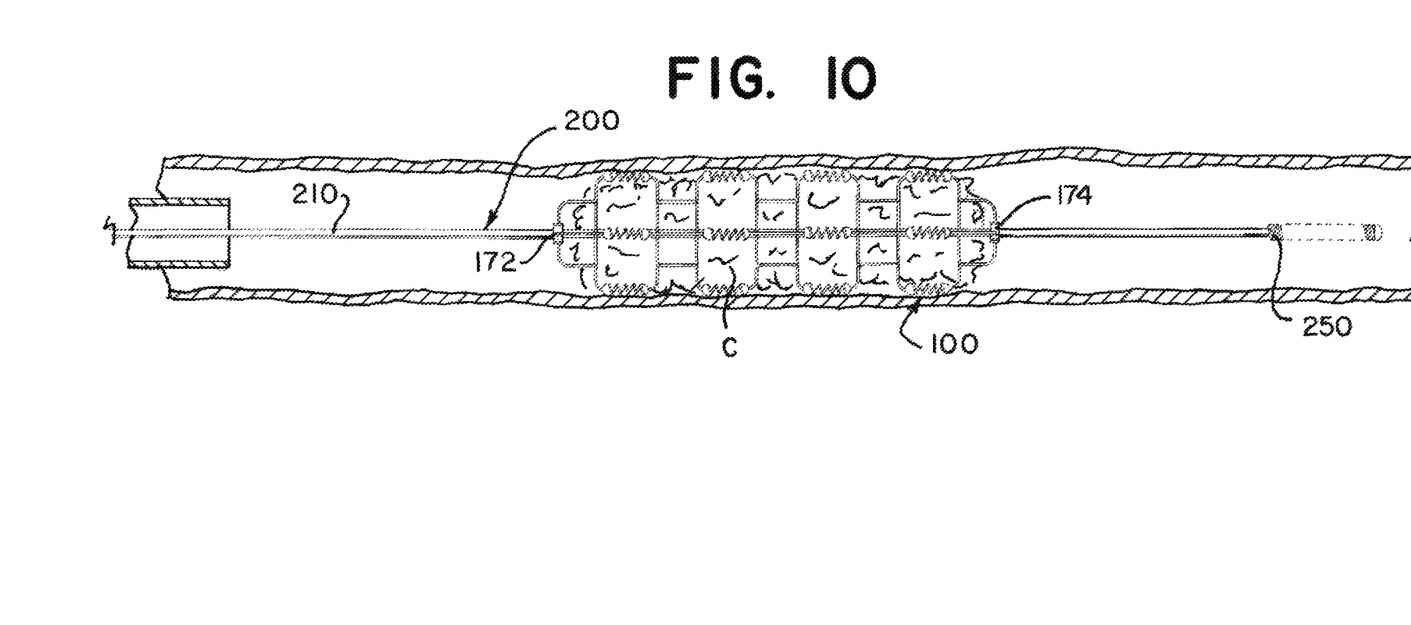
FIG. 10 is an illustration of the intravascular treatment device illustrated in FIGS. 8-9 expanded within the clot.

FIGS. 8 through 10 illustrate an intravascular treatment device 100 capturing a clot C. FIG. 8 illustrates the device 100 collapsed within a microcatheter and being delivered through a blood vessel toward the clot C. FIG. 9 illustrates the microcatheter and device 100 passing through the clot C. FIG. 10 illustrates the microcatheter retracted and the device 100 expanded within the clot C.

The descriptions contained herein are examples of embodiments of the invention and are not intended in any way to limit the scope of the invention. As described herein, the invention contemplates many variations and modifications of the intravascular treatment device, including alternative uses for intravascular treatment, alternative materials, alternative geometries, alternative numbers of components, alternative delivery mechanisms, etc. These modifications would be apparent to those having ordinary skill in the art to which this invention relates and are intended to be within the scope of the claims which follow.

The invention claimed is:

1. An intravascular treatment device comprising:
an elongated guide; and
an expandable framework movable from a collapsed configuration sized to traverse a lumen of a catheter to an expanded configuration sized to extend within a lumen of a blood vessel, the expandable framework comprising:
a plurality of ring struts, each ring strut encircling the elongated guide, and each ring strut movable from a constricted position around the elongated guide when the expandable framework is in the collapsed configuration to a radially expanded position around the elongated guide when the expandable framework is in the expanded configuration;
a plurality of central struts, each central strut joining two adjacent ring struts of the plurality of ring struts such that each ring strut is joined by one or more central struts of the plurality of central struts to only a first adjacent ring strut, each central strut comprising a shape when the expandable framework is in the collapsed configuration that is essentially the same as a shape of the central strut when the expandable framework is in the expanded configuration; and
a plurality of bent struts, each bent strut joining two adjacent ring struts of the plurality of ring struts such that each ring strut is joined by one or more bent struts of the plurality of bent struts to only a second adjacent ring strut opposite the first adjacent ring strut, each of the plurality of bent struts movable from a longitudinally elongated shape when the expandable framework is in the collapsed configuration to a radially expanded shape when the expandable framework is in the expanded configuration, wherein the expandable framework further comprises a proximal end and a distal end, wherein the proximal end is affixed to the elongated guide, and wherein the distal end is slidably movable over the elongated guide.

2. The device of claim 1,
wherein, when the expandable framework is in the expanded configuration,
a first group of bent struts of the plurality of bent struts is positioned to define a first circumference of the expandable framework, and
a first group of central struts of the plurality of central struts are positioned to define a second circumference of the expandable framework measuring smaller than the first circumference.

3. The device of claim 2,
wherein, when the expandable framework is in the expanded configuration,
a second group of bent struts of the plurality of bent struts is positioned adjacent the first group of central struts and is positioned to define a third circumference of the expandable framework about equal to the first circumference, and
a second group of central struts of the plurality of central struts is positioned adjacent the second group of bent struts and is positioned to define a fourth circumference of the expandable framework about equal to the second circumference.

4. The device of claim 3 wherein the first circumference measures more than about two times the second circumference.

5. The device of claim 1 further comprising a plurality of radiopaque markers,
wherein each of the at least a portion of bent struts comprises threads, and
wherein each of the radiopaque makers of the plurality of radiopaque markers are secured to each of the at least a portion of the bent struts by the threads.

6. The device of claim 3 further comprising a plurality of radiopaque markers,
wherein a first group of the plurality of radiopaque markers is positioned on the first group of bent struts to define the first circumference, and wherein a second group of the plurality of radiopaque markers is positioned on the second group of bent struts to define the third circumference.

7. The device of claim 1, wherein, in the expanded configuration, the expandable framework comprises a distal end, a proximal end, a length measurable from the distal end to the proximal end, and a variable circumference that transitions from an first circumference to a second circumference measuring smaller than the first circumference, from the second circumference to a third circumference measuring larger than the second circumference and up to the first circumference, and from the third circumference again to the second circumference along at least a portion of the length of the framework.

8. The device of claim 7,
wherein, in the expanded configuration, third circumference measures smaller than the first circumference, and
wherein, in the expanded configuration, the first circumference is defined by a first group of bent struts of the plurality of bent struts, the second circumference is defined by two adjacent radially expanded ring struts and one or more central struts joining the two adjacent radially expanded ring struts, and the third circumference is defined by a second group of bent struts.

9. An expandable clot capture device movable from a delivery configuration sized to traverse a lumen of a catheter to a deployed configuration sized to extend within a lumen of a blood vessel, the device comprising:
a plurality of ring struts, each ring strut movable from a constricted circumference when the clot capture device is in the delivery configuration to an expanded circumference when the clot capture device is in the deployed configuration;
a plurality of central struts, each central strut comprising a shape when the clot capture device is in the delivery configuration that is essentially the same as a shape of the central strut when the clot capture device is in the deployed configuration;
a plurality of bent struts, each of the plurality of bent struts movable from a longitudinally elongated shape when the device is in the delivery configuration to a radially expanded shape when the clot capture device is in the deployed configuration;
an expandable frame comprising the plurality of ring struts, the plurality of central struts, and the plurality of bent struts; and
a guide wire extending through a central axis of the expandable frame and affixed to the expandable frame at a singular node approximate a proximal end of the expandable frame,
wherein at least a portion of the plurality of ring struts are each joined to a first adjacent ring strut and a second adjacent ring strut opposite the first adjacent ring strut,
wherein each of the at least a portion of the plurality of ring struts are joined to the associated first adjacent ring strut by one or more central struts of the plurality of central struts,
wherein each of the at least a portion of the plurality of ring struts are joined to the second adjacent ring strut by a group of one or more bent struts of the plurality of bent struts,
wherein when the clot capture device is in the deployed configuration, each group of the one or more bent struts defines a respective circumference, and
wherein when the clot capture device is in the deployed configuration the expanded circumference of each ring strut measures smaller than each respective circumference of each group of the one or more bent struts.

10. The expandable clot capture device of claim 9,
wherein when the clot capture device is in the deployed configuration a first group of one or more bent struts defines a first circumference, a second group of one or more bent struts defines a second circumference approximately equal to the first circumference, and a third group of one or more bent struts positioned distal the first group and proximal second group comprises a third circumference measuring smaller than the first circumference and the second circumference and measuring larger than the expanded circumference of each ring strut.

11. The expandable clot capture device of claim 9,
wherein each of the at least a portion of the plurality of ring struts is separated from each first adjacent ring strut by a first distance when the clot capture device is in the delivery configuration and a second distance when the clot capture device is in the deployed configuration, the first distance being approximately equal to the second distance, and
wherein each of the at least a portion of the plurality of ring struts is separated from each second adjacent ring strut by a third distance when the clot capture device is in the delivery configuration and a fourth distance when the clot capture device is in the deployed configuration, the third distance being greater than the fourth distance.

12. The expandable clot capture device of claim 9 further comprising a plurality of radiopaque markers, wherein at least a portion of the bent struts comprises a radiopaque marker of the plurality of radiopaque markers attached thereto,
wherein the plurality of radiopaque markers provides an indication of a collapsed circumference of the clot capture device when the clot capture device is in the delivery configuration and an expanded circumference of the clot capture device when the clot capture device is in the deployed configuration.

13. The expandable clot capture device of claim 12 wherein each of the at least a portion of bent struts comprises threads and each of the radiopaque makers of the plurality of radiopaque markers are secured to each of the at least a portion of the bent struts by the threads.

14. A method comprising:
positioning an expandable frame to encircle a guide wire;
attaching the frame to the guide wire at an attachment site approximate a proximal end of the frame;
collapsing the frame around the guide wire such that the frame is in a delivery configuration sized to traverse a lumen of a catheter;
expanding the frame from the delivery configuration to a deployed configuration;
maintaining the attachment of the frame to the guide wire at the attachment site as the frame expands from the delivery configuration to the deployed configuration;
sliding at least a portion of the frame over the guide wire as the frame expands from the delivery configuration to the deployed configuration; and
shaping the frame in the deployed configuration, to comprise a length measurable from the distal end to the proximal end, and a variable circumference that transitions from an first circumference to a second circumference measuring smaller than half the first circumference, from the second circumference to a third circumference measuring larger than the second circumference and up to the first circumference, and from the third circumference again to the second circumference along at least a portion of the length of the frame.

15. The method of claim 14 further comprising:

forming the frame from a plurality of ring struts, a plurality of longitudinal struts, and a plurality of bendable struts;

positioning each ring strut to encircle the guide wire;

spacing the plurality of ring struts along a length of the frame such that each ring strut has a first adjacent neighboring ring strut and a second adjacent neighboring ring strut;

connecting each ring strut to its first adjacent neighboring ring strut by one or more longitudinal struts of the plurality of longitudinal struts;

connecting each ring strut to its second adjacent neighboring ring strut by one or more bendable struts of the plurality of bendable struts, and wherein the step of expanding the frame from the delivery configuration to the deployed configuration further comprises:

expanding each ring strut of the plurality of ring struts radially away from the guide wire as the frame expands from the delivery configuration to the deployed configuration;

maintaining an essentially constant shape of each longitudinal strut of the plurality of longitudinal struts as the frame expands from the delivery configuration to the deployed configuration, the shape of each longitudinal strut when the frame is in the delivery configuration being essentially unchanged after the frame is in the deployed configuration; and extending each bendable strut of the plurality of bendable struts radially away from the guide wire as the frame expands from the delivery configuration to the deployed configuration.

16. The method of claim 14 further comprising:

expanding at least a portion of the frame within a clot; and capturing at least a portion of the clot within the frame.

17. The method of claim 14 further comprising:

positioning a plurality of radiopaque markers to provide an indication of the first circumference and the third circumference when the frame is in the deployed configuration.

* * * * *